United States Patent [19]

Geller

[11] Patent Number: 4,469,443
[45] Date of Patent: Sep. 4, 1984

[54] ATMOSPHERIC TRANSMISSOMETER

[75] Inventor: Myer Geller, San Diego, Calif.

[73] Assignee: The United States of America as represented by the Secretary of the Navy, Washington, D.C.

[21] Appl. No.: 383,867

[22] Filed: Jun. 1, 1982

[51] Int. Cl.³ .............................................. G01J 4/00
[52] U.S. Cl. ................................... 356/364; 356/434; 356/437
[58] Field of Search ............... 356/364, 365, 368, 434, 356/437, 438; 350/388; 250/564, 565, 575, 225

[56] References Cited

U.S. PATENT DOCUMENTS

| | | | |
|---|---|---|---|
| 2,849,912 | 9/1958 | Plesse et al. | 356/408 |
| 3,560,098 | 2/1971 | Witte et al. | 356/434 |
| 3,772,525 | 11/1973 | Goodwin | 250/565 |
| 3,784,307 | 1/1974 | Jackson et al. | 356/51 |
| 4,001,595 | 1/1977 | Reisman | 250/565 X |

FOREIGN PATENT DOCUMENTS 796661 6/1958 United Kingdom ................ 356/434

Primary Examiner—Davis L. Willis
Assistant Examiner—Matthew W. Koren
Attorney, Agent, or Firm—Robert F. Beers; Ervin F. Johnston; Edmund W. Rusche, Jr.

[57] ABSTRACT

An apparatus and method is described for separately measuring the optical intensities of the following: a sample beam having traversed a sample medium; a backscattered beam having been backscattered by the sample medium; a composite beam composed of the sample beam plus a reference beam having traversed a reference medium; and a second composite beam composed of the backscattered beam plus the reference beam. Measurements of these parameters is accomplished through the use of a linearly polarized source beam whose plane of polarization may be rotated between two orthogonal planes. The source beam is split into the sample and reference beams. The plane of polarization of the sample beam is caused to be rotated 90° from the plane of polarization of the backscattered beam after interaction with the sample medium. The plane of polarization of the reference beam is selectively controlled between two orthogonal planes such that when combined with the sample beam and backscattered beam a polarization analyzer will allow passage of only those portions with a preselected plane of polarization for measurement and analysis of the light intensity. From the various measured intensities available the visibility or transmissivity of a sample medium may be determined. The sample medium may be isolated from the remainder of the transmissometer by a window which will allow unaltered transmission of the sample beam and the backscattered beam from the sample medium. With this configuration the invention may be utilized in an airborne manner, mounted on an airplane for the purpose of measuring transmissivity of atmospheric conditions in clouds.

24 Claims, 7 Drawing Figures

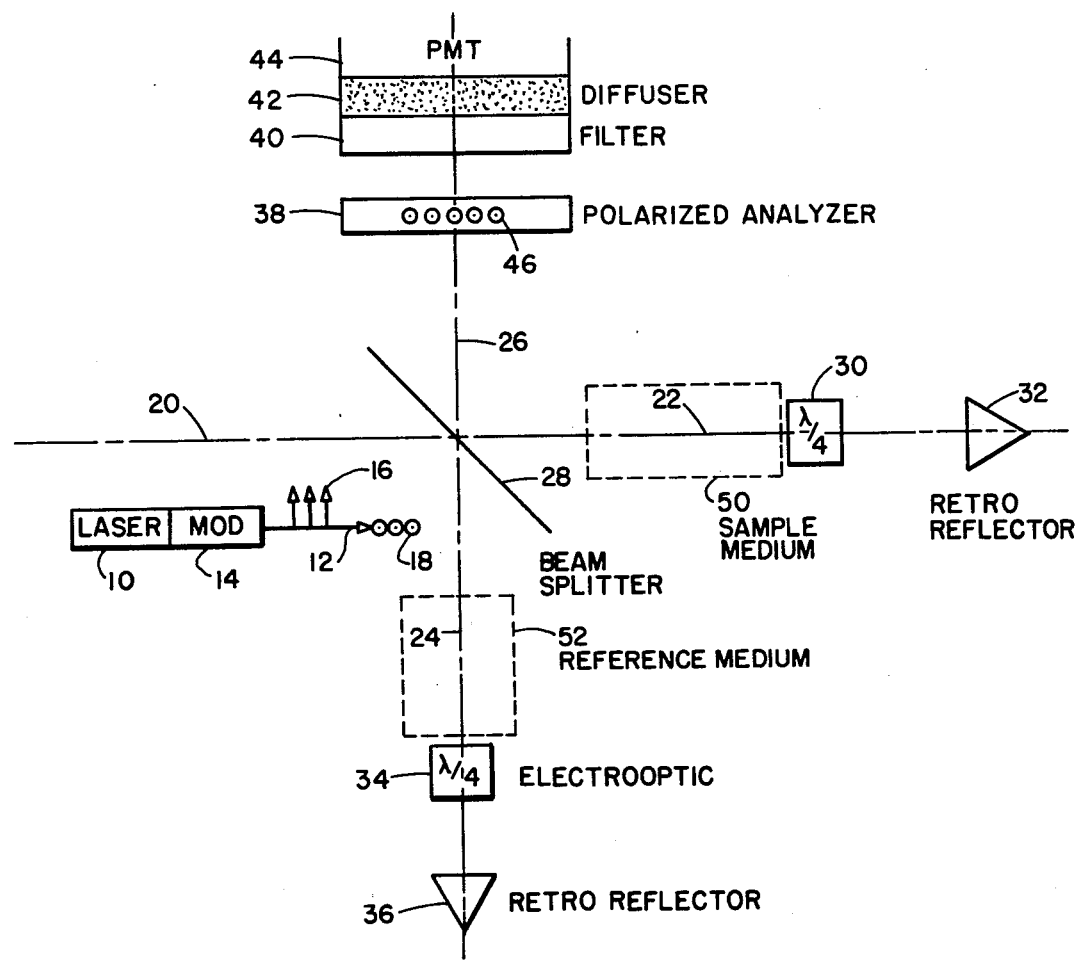
FIG. 1 TRANSMISSOMETER
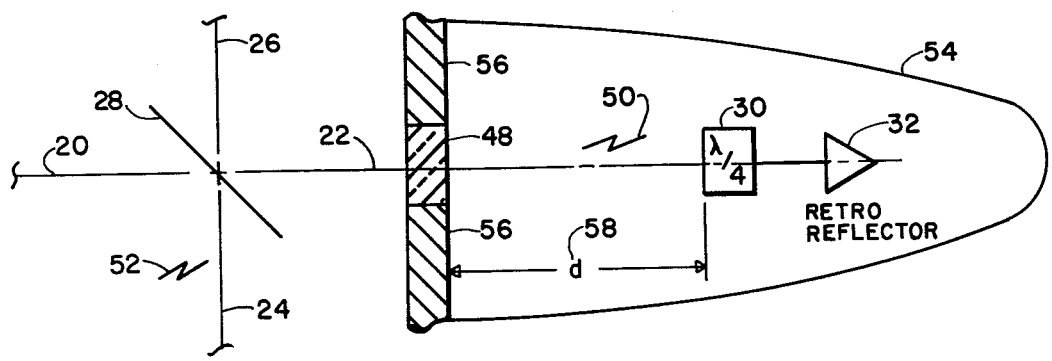
FIG. 2 AIRBORNE TRANSMISSOMETER

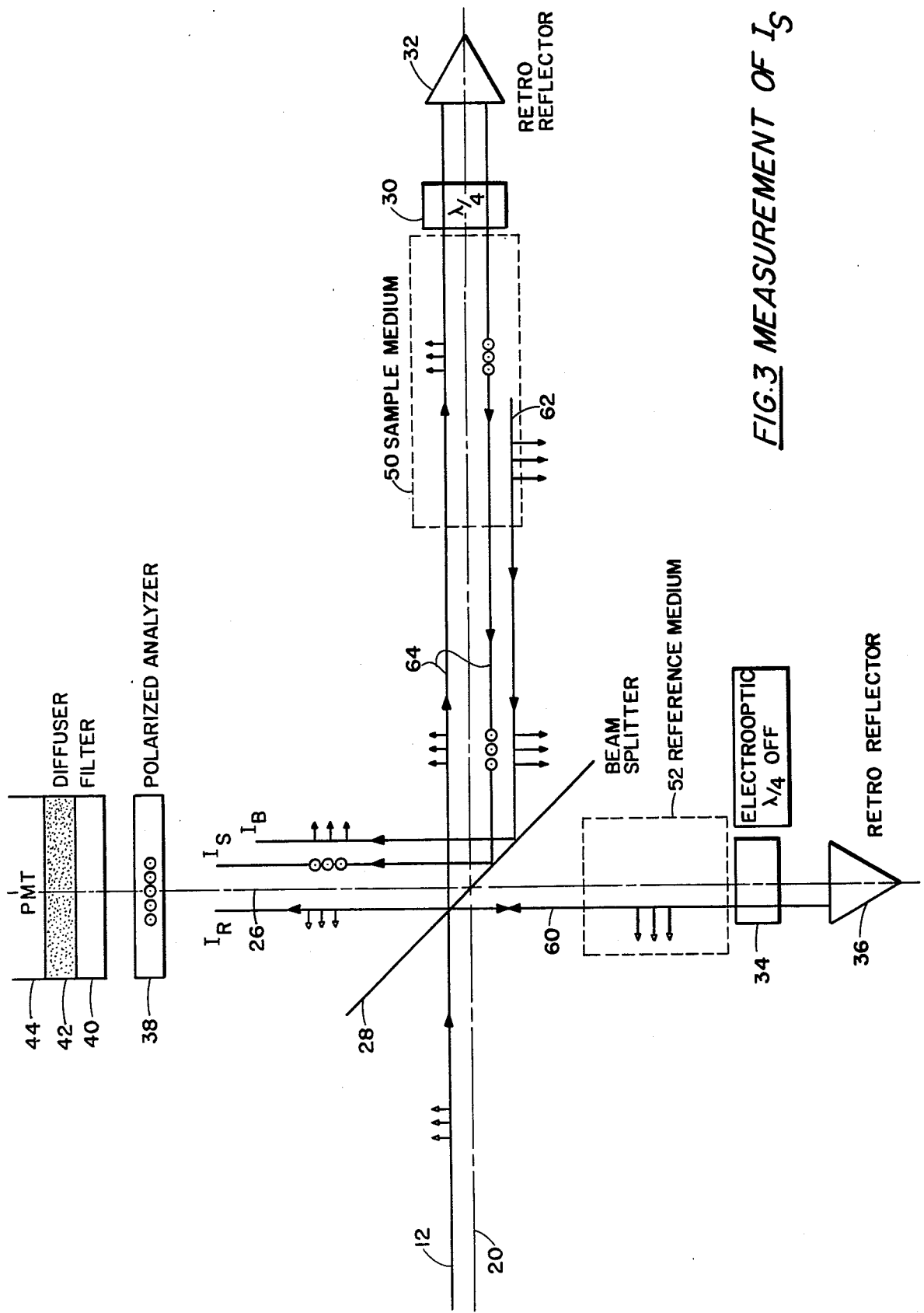
FIG.3 MEASUREMENT OF $I_S$

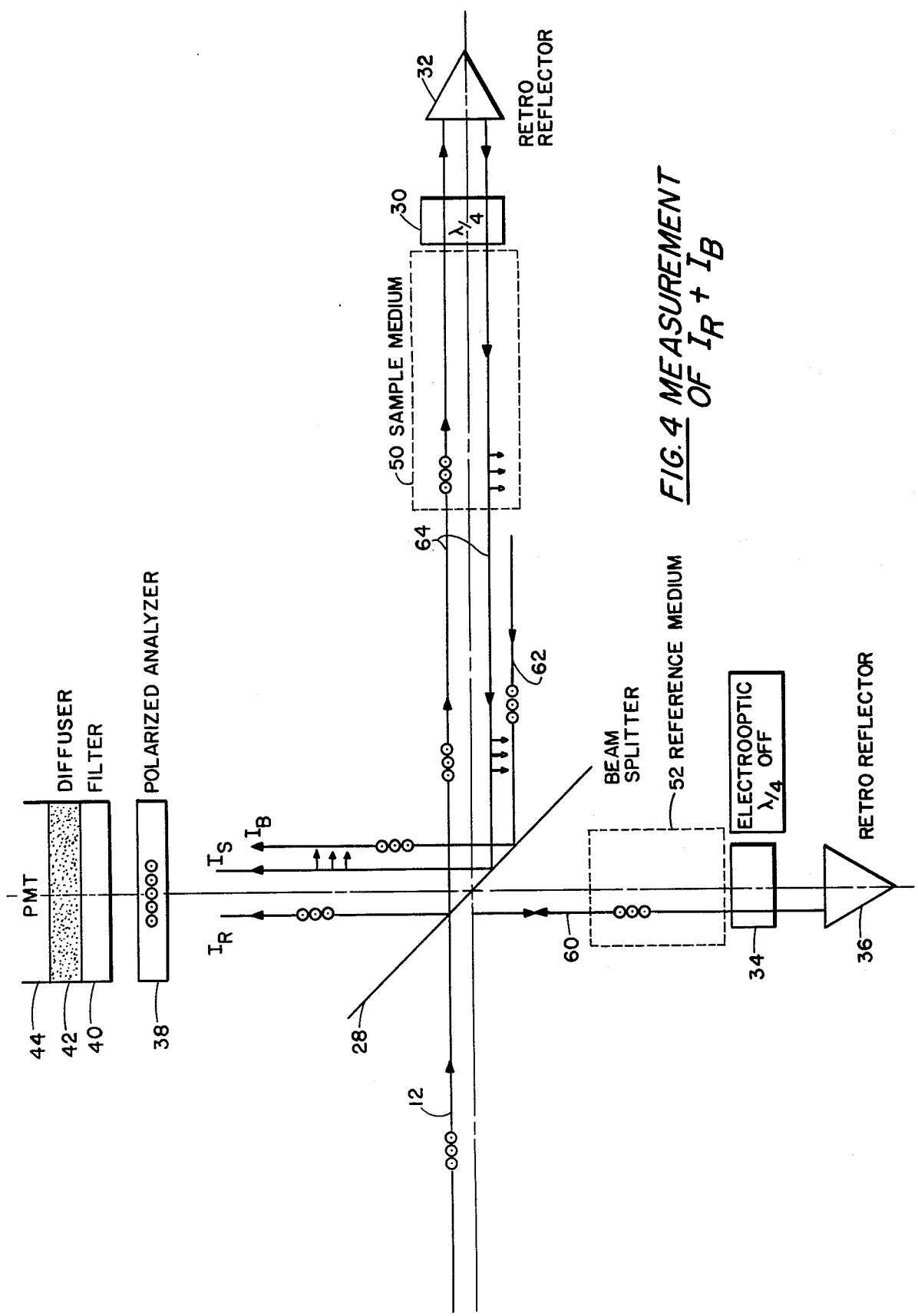

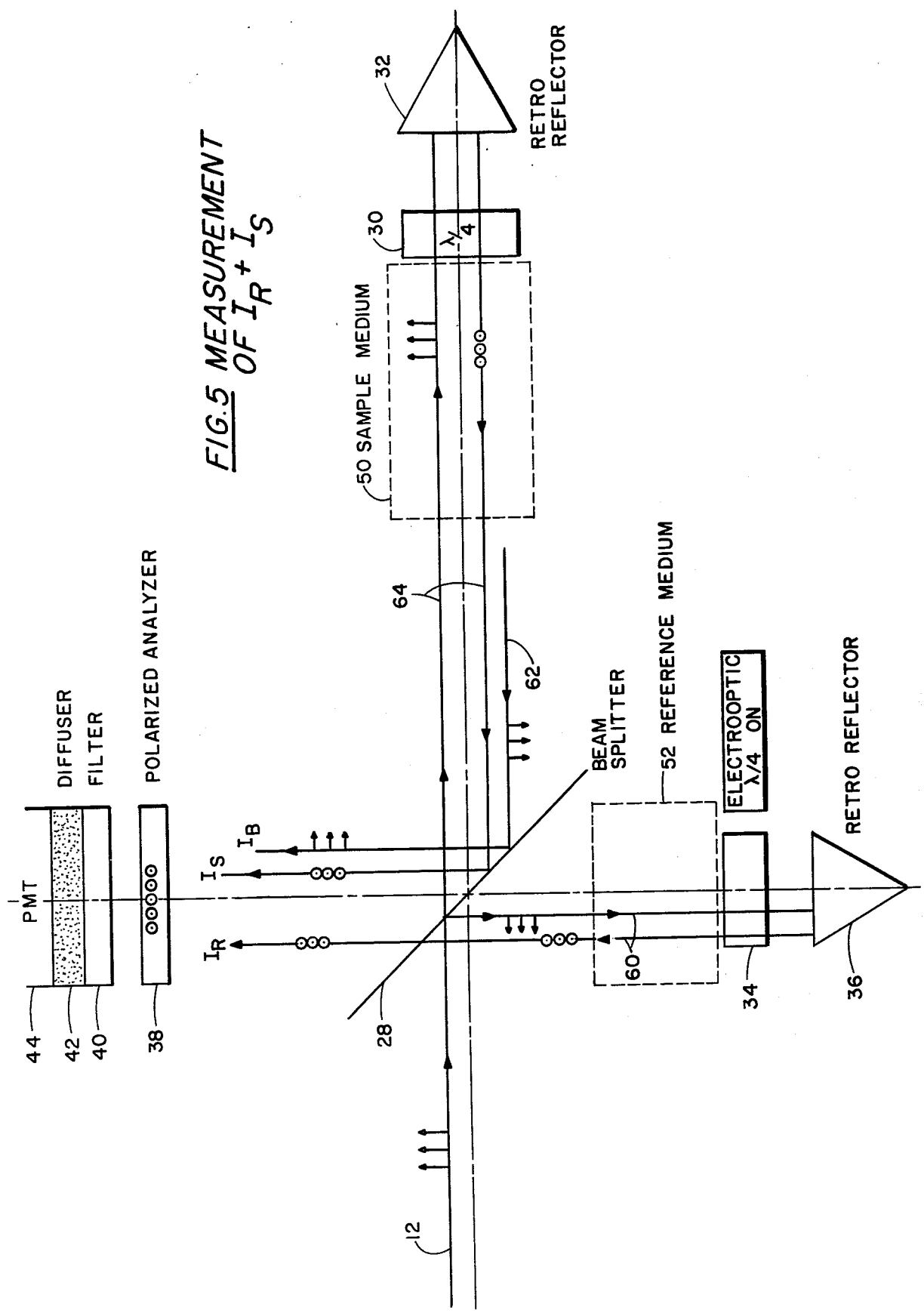

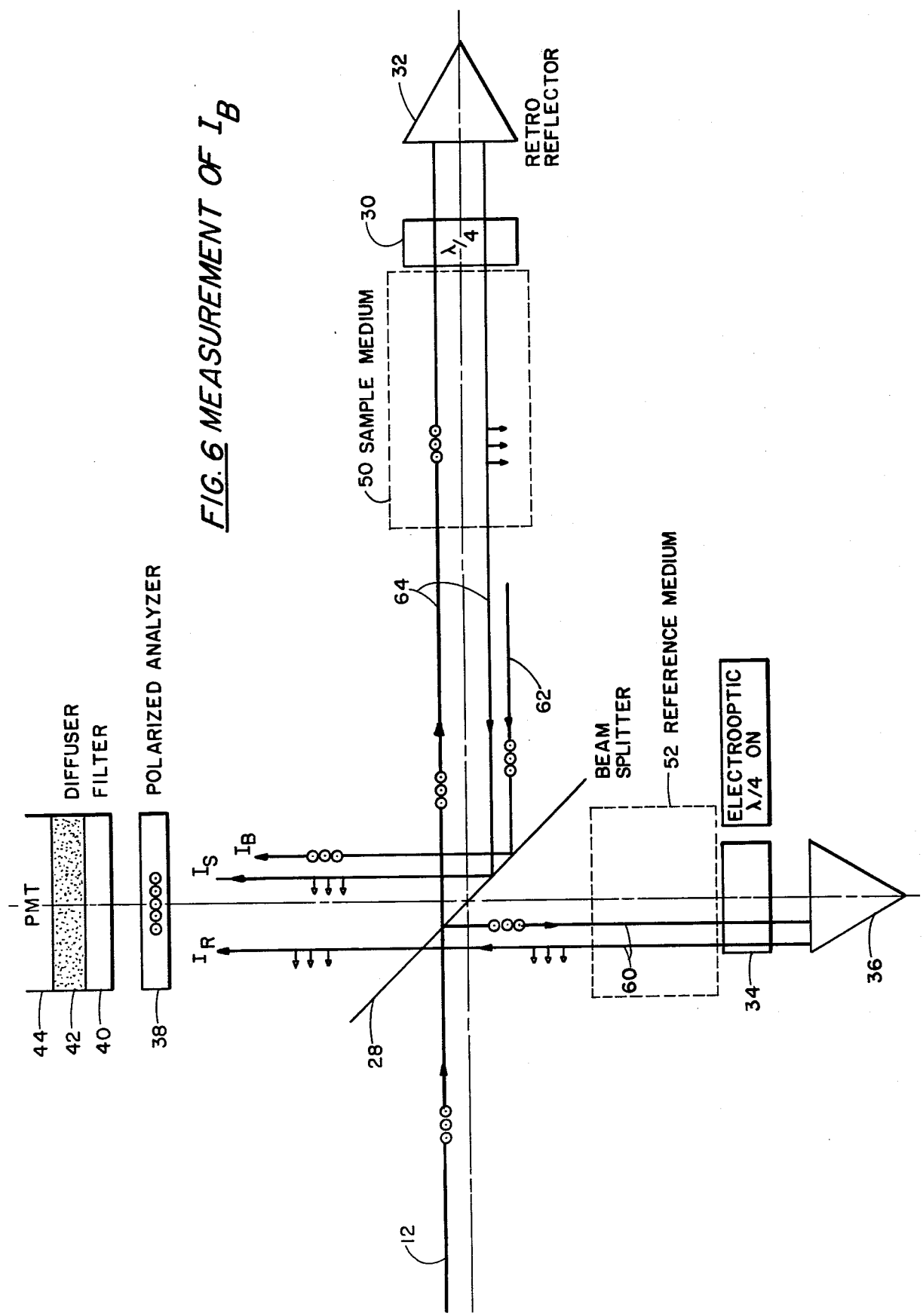

FIG. 7 MODULATION CYCLE

| SOURCE BEAM PLANE OF POLARIZATION (Duty Cycle = $f_o$) | ELECTROOPTIC QUARTER-WAVE PLATE STATUS (Duty Cycle = $f_o/2$) | INTENSITY MEASURED | REF. FIG. |
|---|---|---|---|
| p | OFF | $I_S$ | 3 |
| s | OFF | $I_R + I_B$ | 4 |
| p | ON | $I_R + I_S$ | 5 |
| s | ON | $I_B$ | 6 |

ATMOSPHERIC TRANSMISSOMETER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The knowledge of atmospheric visibility is of great importance to the U.S. Government and to the air travel industries. Visibility is measured by a transmissometer which measures a transmissivity, or the related property, the absorption of light by the atmosphere.

Light beams traversing atmospheric paths are subject to absorption and scattering. The intensity of light beams, and consequently the visibility, traversing atmospheric paths is reduced by absorption and scattering. Absorption is generally created by the molecular and particle components of the atmosphere physically capturing energy from the traversing light and is often the major cause for reducing intensity. However, diffuse and specular scattering of light energy can become quite significant when the atmosphere contains particulate matter. The greater the absorption and scattering, the less is atmospheric visibility.

Transmissometers are in use at airports to measure the visibility. The usual arrangement is the transmission of a beam of light from a source with a known intensity over a path length of a given distance to a receiving photoelectric cell. The output of the photoelectric cell measures the light received and provides a measure of the atmospheric absorption or the transmissivity. Other transmissometers have measured the difference in intensity of a light beam transmitted over two different path lengths and from these measurements the transmissivity or absorption is calculated.

In addition, photometric techniques have been available to make measurements of transmittance, absorptance or reflectance of a sample medium. Usually, such measurements are made relative to a reference medium and have not been generally applied to visibility oriented measurements in the atmosphere, particularly, in situ measurements in clouds.

Although the above methods have capability for in situ operations none have been found to be applied for airborne measurements of the transmissivity of the atmosphere.

SUMMARY OF THE INVENTION

An apparatus and method is disclosed for measuring the intensity of a light beam that has traversed a sample medium, $I_S$, the intensity of a light beam that has been scattered back upon itself from the sample medium, $I_B$, and the intensity of the portion of a light beam that has traversed a reference medium, $I_R$. Specifically, a transmissometer based on this invention measures $I_S$, $I_B$, $I_S+I_R$, and $I_R+I_B$. The ability to make the above measurements is based upon the use of polarized light and the control of the planes of polarization for the respective light beams.

The apparatus receives a collimated, linearly polarized source beam of light with the plane of polarization preset in one of two orthogonal planes, each plane parallel to the direction of propagation. The source beam is split by a beam splitter into two beams, a beam directed toward the sample medium and a reference beam. The sample medium physically splits the beam directed toward the sample medium into two further beams, a beam backscattered upon itself with intensity $I_B$, and a beam traversing the sample medium with the result intensity $I_S$. The sample beam traversing the sample medium then proceeds through a quarter-wave plate to a reflector which reflects the beam back upon itself again through the quarter-wave plate and the sample medium to the beam splitter. The quarter-wave plate causes a total rotation of the plane of polarization for the sample beam of 90°. This makes the sample beam's plane of polarization perpendicular to the backscattered beam's plane of polarization.

The reference beam traverses a reference medium and an electrooptical quarter-wave plate onto a reflector which reflects it back upon itself. Then, it again traverses in reverse the electrooptical quarter-wave plate, the reference medium and returns to the beam splitter. The electrooptical quarter-wave plate provides a controlled, selective means to rotate the plane of polarization of the reference beam into one of two orthogonal planes parallel to the direction of propagation.

The three beams, the sample beam, the backscattered beam and the reference beam, all meet at the beam splitter and are combined by the beam splitter into a single combined and collimated beam. This combined beam contains the three beams in their particular states of polarization. The combined beam impinges upon a polarized analyzer which allows through only that portion of the combined beam which has a plane of polarization aligned with the axis of polarization of the analyzer. This has the effect of blocking out select unwanted beams and allowing to pass that portion of the beam which is desired to be measured.

Following the polarized analyzer the passed beam may be bandpass filtered to control the optical bandwidth of interest and may impinge upon a diffuser to spread the light pattern uniformly over a controlled surface for detection by a photomultiplier tube. Following this, the signal from the photomultiplier tube may be fed to standard electronic means for measuring and displaying the magnitude of the intensity of the detected beam.

The resulting measurements are summarized as follows: when the plane of polarization of the sample beam is perpendicular to the planes of polarization of the reference beam and the backscattered beam, then measurement of the intensity of the sample beam, $I_S$, or of the combined intensities of the reference beam and the backscattered beam, $I_R+I_B$, is accomplished when the respective planes of polarization are aligned with the set axis of polarization of the analyzer; when the plane of polarization of the backscattered beam is perpendicular to both the plane of polarization of the sample beam and the reference beam, then measured is the intensity of the backscattered beam, $I_B$, or the intensity of the combined sample beam and reference beam, $I_S+I_R$, again depending upon the alignment of the respective planes of polarization with the axis of polarization of the analyzer. It should be noted that at all times of measurement, the planes of polarization for the backscattered beam and the sample beam will be orthogonal to each other.

The apparatus and method of this invention are readily suitable for in situ operation; for example, use in an airplane for airborne measurement of cloud visibility or absorption characteristics.

OBJECTS OF THE INVENTION

An object of the invention is to provide an apparatus and method using plane-polarized light beams for measurement of light intensities important in determining the visibility of a sample atmosphere.

A second objective is the determination, using plane-polarized light beams, of the light intensities for the backscattered light from a sample atmosphere, $I_B$, the transmitted light through the sample atmosphere, $I_S$, and the transmitted light through a reference medium, $I_R$.

Another objective is the application of modulating techniques to control the rotation of the planes of polarization of the source beam, the sample beam, and the reference beam in an automated manner for specifically measuring the intensities $I_S$, $I_B$, $I_S+I_R$, and $I_R+I_B$.

Still another objective is the use of the apparatus and method on an airplane for in situ airborne measurements of these intensities for clouds and other atmospheric conditions.

Other objects, features and advantages of the present invention will become more apparent in the light of the following detailed description of a preferred embodiment thereof as illustrated in the accompanying drawings.

BRIEF DESCRIPTION OF THE DRAWINGS

FIG. 1 is a schematic layout of a preferred embodiment of the transmissometer.

FIG. 2 is a schematic layout of the invention applied as an airborne transmissometer.

FIG. 3 is a schematic layout of the invention showing the propagation and polarization of the various light beams for the method of measuring the intensity $I_S$.

FIG. 4 is a schematic layout of the invention showing the propagation and polarization of the various light beams for the method of measuring the intensity $I_R+I_B$.

FIG. 5 is a schematic layout of the invention showing the propagation and polarization of the various light beams for the method of measuring the intensity of $I_R+I_S$.

FIG. 6 is a schematic layout of the invention showing the propagation and polarization of the various light beams for the method of measuring the intensity $I_B$.

FIG. 7 is a modulation cycle table showing the intensity measured as a function of the modulation status of the planes of polarization for the source beam and the ON/OFF status of the electrooptical quarter-wave plate.

DESCRIPTION OF THE PREFERRED EMBODIMENT

A general layout of a preferred embodiment of the invention is shown in FIG. 1. The helium-neon laser 10 at 632.8 nm provides a source for a collimated, linearly polarized source beam 12 of light. Other sources, particularly laser sources, may be equally satisfactory for providing the source beam of light at other wavelengths of interest. The plane of polarization of the source beam is modulated at a frequency $f_o$ by a modulator 14 to switch alternatively between two orthogonal planes 16 and 18, parallel to the source beam axis 20, or the direction of propagation. The orthogonal planes of polarization for the modulated source beam, as well as for all other beams to be discussed later, are represented in all figures as arrows drawn with tips shown in the plane of the figure to identify when the polarization of a beam is oriented parallel to the plane of the FIG. 16, or with circles containing dots at their centers to identify when the polarization of a beam is oriented perpendicular to the plane of the FIG. 18. Orientation of the source beam plane of polarization may be accomplished by manual switching or other equivalent means rather than by atuomated modulation as suggested here.

Also shown in FIG. 1 is the source beam axis 20, a sample beam axis 22 which is colinear to the source beam axis, a reference beam axis 24, and a detector path axis 26 which is colinear to the reference beam axis. Each axis is separated from the others by a beam splitter 28 and, in this preferred embodiment, the detector path axis and the reference beam axis are perpendicular to the source beam axis and the sample beam axis.

The beam splitter 28 is inserted to serve two functions. First, it splits source beam 12 into two beams, one beam directed along the sample beam axis and the second directed along the reference beam axis. Second, it combines beams returning along these axes into a combined beam directed along the detector path axis. In other embodiments these functions of splitting the source beam and combining the returning beams may be accomplished by independent or separate means.

A quarter-wave plate 30 and a retroreflector 32 are located on the sample beam axis at the end opposite the beam splitter. An electrooptical quarter-wave plate 34 and a second retroreflector 36 are located on the reference beam axis at the end opposite the beam splitter. Clearly, any means for reflecting beams of polarized light may be substituted for either retroreflector.

The quarter-wave plates 30 and 34 are to cause a 90° total rotation of the plane of polarization of any light beam traversing either of them both before and after reflection by the retroreflectors. While this rotation occurs naturally with quarter-wave plate 30, the electrooptical quarter-wave plate 34 will only cause rotation when it is turned on by any standard source of high voltage. In the automated configuration of this embodiment, the ON/OFF control of the electrooptical quarter-wave plate is modulated at a frequency $\frac{1}{2} f_o$ which is synchronized with the modulation of the source beam.

A polarized analyzer 38, a bandpass filter 40, a diffuser 42, and a photomultiplier tube (PMT) 44 are located at the end of the detection path axis opposite the beam splitter. This provides uniformity of measurement since one detector measures all beams.

The bandpass filter controls the frequency bandwidth of the light to be detected. Its use is optional depending upon the requirements of any specific measurement.

The polarized analyzer only permits passage of that portion of a light beam with a plane of polarization aligned parallel with the polarization axis of the analyzer. In FIGS. 1 and 3-6, the analyzer's axis of polarization is shown oriented perpendicular to the plane of the figure as represented by the circles marked with their centers, 46.

The diffuser spreads a beam of light over a predetermined area to optimize the detection capability of the PMT. Following detection by the PMT, an electrical signal from it may be fed to any of several standard electronic circuits for analyzing and displaying the magnitude of the measured light intensities.

FIG. 2 shows an embodiment adapted for airborne use in clouds and other atmospheric conditions. Functionally, in any embodiment, a window 48 may be inserted at the beam splitter end of the sample beam axis to facilitate insulation of the sample medium 50 from the reference medium 52 and the remainder of the transmissiometer. Specifically for airborne measurements, the transmissometer is installed inside an airplane in a manner where the sample beam axis with its respective quarter-wave plate 30 and retroreflector 32 are mounted on the wing 54 of the plane, outside of the window 48 and fuselage 56.

The quarter-wave plate 30 and retroreflector 32 should be mounted at distance d, 58, such that the modulation frequency $f_o$ is sufficiently low to readily permit the switching of the kilovolts of voltage necessary for activating the electrooptical quarter-wave plate and yet high enough to allow treatment of the cloud as being homogeneous over the distance that the aircraft travels in a time of $\frac{1}{2} f_o$. In this embodiment the quarter-wave plate and retroreflector mounted on the wing must be heated in order to avoid condensation of moisture upon their surfaces.

Additionally, it is proposed that the photomultiplier be provided with an S-11 surface if the source is the helium-neon laser. The diffuser may be made of ground glass. The helium-neon laser may be operated at a frequency of 6328 anstroms thereby also identifying the center frequency for the bandwidth of the filter.

FIGS. 3 through 6 show the methods of operation through the various states of the planes of polarization for a reference beam 60, source beam 12, a backscattered beam 62, and a sample beam 64. FIG. 3 schematically shows the method for measurement of the intensity of the sample beam, $I_S$.

For this method the plane of polarization of source beam 12 is in the plane of the figure. The plane of polarization of sample beam 64 as it traverses the sample medium for the first time is also in the plane of the figure. As the sample beam traverses quarter-wave plate 30, is reflected by the retroreflector 32, and returns to traverse the quarter-wave plate a second time its plane of polarization is rotated 90° placing it perpendicular to the plane of the figure. The plane of polarization of backscattered beam 62 remains the same as the plane of polarization of sample beam 64 prior to passage through the sample medium, i.e., in the plane of the figure.

The plane of polarization for reference beam 60, split from source beam 12, as it traverses the reference medium is in the plane of the figure. As the reference beam traverses the electrooptic quarter-wave plate 34, is reflected by the retroreflector 36, and returns through the electrooptic quarter-wave plate its plane of polarization remains in the plane of the figure because the electrooptic quarter-wave plate has been turned off and is therefore incapable of rotating the plane of polarization.

The combination of the three beams occurs at the beam splitter for the embodiment shown. In other embodiments, combination may occur at a common place where the three beams are selectively directed to return. At this point the planes of polarization for the backscattered beam and the reference beam are parallel and in the plane of the figure while the plane of polarization of the sample beam is perpendicular to these and the plane of the figure. The axis of polarization for the polarized analyzer has been set perpendicular to the plane of the figure thereby allowing only the sample beam to pass while simultaneously blocking transmission of the reference beam and the backscattered beam. Consequently, the PMT 44 and measuring circuit only receive and measure the intensity of the sample beam, $I_S$.

FIG. 4 schematically shows the method for measuring the combined intensities of reference beam 60 and backscattered beam 62, $I_R + I_B$. The source beam 12 has a plane of polarization established perpendicular to the plane of the figure. The sample beam 64 passed through beam splitter 28 from the source beam maintains this plane of polarization as it passes through sample medium 50 for the first time. After the sample beam has traversed the quarter-wave plate 30, been reflected by the retroreflector 32, and retraversed the quarter-wave plate its plane of polarization, as before, has been rotated 90° and now is parallel to the plane of the figure. The backscattered beam maintains a plane of polarization perpendicular to the plane of the figure. Since electrooptic quarter-wave plate 34 is again in the OFF condition the reference beam plane of polarization will remain perpendicular to the plane of the figure and parallel with the source beam's plane of polarization.

Upon recombination of the three beams, the planes of polarization for the reference beam and the backscattered beam are perpendicular to the plane of the figure while the plane of polarization of the sample beam is parallel to the plane of the figure. Since the axis of polarization for the polarized analyzer is set perpendicular to the plane of the figure, only the combination of the reference beam and the backscattered beam is allowed to pass while the sample beam is blocked. Therefore, PMT 44 and the measuring circuit will measure the combined intensity of the reference beam and the backscattered beam, $I_R + I_B$.

FIG. 5 schematically shows the method for measuring the combined intensities of reference beam 60 and sample beam 64, $I_{R+IS}$. Here source beam 12 has a plane of polarization parallel to the plane of the figure. The sample beam maintains this plane of polarization as it traverses the sample medium for the first time. Again after passage through quarter-wave plate 30, reflection by the retroreflector, and return passage through the quarter-wave plate the sample beam has its plane of polarization rotated by 90°. The backscattered beam 62 maintains a plane of polarization parallel to the plane of the figure.

In this method electrooptic quarter-wave plate 34 in the reference beam path has been turned ON. Therefore reference beam 60, when reflected by beam splitter 28 from the source beam has a plane of polarization parallel to the plane of the figure, but after traversing quarter-wave plate 34, being reflected by the retroreflector 36 and retraversing the quarter-wave plate its plane of polarization has been rotated 90°. The reference beam returns to the beam splitter now with its plane of polarization perpendicular to the plane of the figure.

The combined beams now have their planes of polarization oriented such that the reference and sample beam's planes are perpendicular to the plane of the figure and the backscattered beam's plane is parallel to the plane of the figure. With the axis of polarization for the polarized analyzer perpendicular to the plane of the figure, only the reference beam combined with the source beam will be allowed to pass through to the PMT while the backscattered beam will be blocked from passage. Therefore, the PMT 44 will measure the combined intensities of the sample beam and the reference beam, $I_S + I_R$.

FIG. 6 schematically shows the method for measuring the intensity of backscattered beam 62, $I_B$. Here, source beam 12 starts with its plane of polarization perpendicular to the plane of the figure. The sample beam 64 also has its plane of polarization perpendicular to the plane of the figure as it traverses sample medium 50 for the first time. Again following its interaction with quarter-wave plate 30 and the retroreflector 32, its plane of polarization has been rotated 90° to become parallel to the plane of the figure. The backscattered beam's plane of polarization is, of course, perpendicular to the plane of the figure.

For this method electrooptic quarter-wave plate 34 is again turned ON. Consequently, reference beam 60 with its initial plane of polarization perpendicular to the plane of the figure will have its plane of polarization rotated 90° after interaction with the electrooptic quarter-wave plate and retroreflector.

The combined beams now line up such that the reference beam and the sample beam have their planes of polarization parallel to the plane of the figure while the backscattered beam has its plane of polarization perpendicular to the figure. The polarized analyzer will thus only allow passage of the backscattered beam while blocking passage of the other two beams. Therefore, the PMT 44 and measuring circuit will now measure the intensity of the backscattered beam, $I_B$.

FIG. 7 is a table showing the status during each method of measurement for the plane of polarization of the source beam and the status of electrooptic quarter-wave plate 34 which controls the plane of polarization of the reference beam. A "p" under the column Source Beam Plane of Polarization represents polarization parallel to the plane of the figure. An "s" in that same column represents the plane of polarization of the source beam perpendicular to the plane of the figure. In the column Electrooptic Quarter-Wave Plate Status, ON and OFF represent periods when the electrooptic quarter-wave plate is, or is not, activated to cause rotation of the reference beam plane of polarization by 90°. The third column, Intensity Measured, lists the value of intensity that is measured for the conditions shown on each horizontal line. Each horizontal line represents the method shown in FIGS. 3-6 sequentially.

With a duty cycle $f_o$ applied to the modulation of the source beam plane of polarization, it is to be noted that the plane of polarization of the source beam rotates through two complete cycles while the plane of polarization of the reference beam rotates through one cycle. In addition, it is clear that redundancy in measurements is present, i.e., there are four measurements to determine three unknowns. This has the advantage of providing an internal check on the system.

Obviously, many modifications and variations of the present invention are possible in the light of the above teachings. It is therefore to be understood that within the scope of the appended claims the invention may be practiced otherwise than as specifically described.

What is claimed is:

1. An apparatus for the selective measurement of the optical intensities of a sample beam having traversed a sample medium, a backscattered beam having been backscattered by the sample medium, a first composite beam composed of the sample beam plus a reference beam having traversed a reference medium, and a second composite beam composed of the backscattered beam plus the reference beam, which comprises:

means disposed to receive a collimated, linearly polarized source beam for selectively switching the plane of polarization between two orthogonal planes each parallel to the line of propagation of the source beam;

means disposed to receive the polarized source beam for splitting it into two beams, the first beam being further physically divided into the backscattered beam and the sample beam as it traverses the sample medium, and the second beam becoming the reference beam as it traverses the reference medium;

means disposed to receive the sample beam for rotating its plane of polarization 90° from the plane of polarization of the backscattered beam;

means disposed to receive the reference beam for selectively aligning its plane of polarization parallel to the plane of polarization of either the sample beam of the backscattered beam;

separate means disposed to receive the backscattered beam, the sample beam, and the reference beam for redirecting their directions of propagation to converge at a common place;

means disposed to receive the redirected sample, backscattered, and reference beams at the common place for combining them to form a colinear, collimated combined beam;

means disposed to receive the combined beam for polarization-analyzing it to transmit only that portion with the plane of polarization aligned in a predetermined direction; and means disposed to receive the transmitted portion of the combined beam for detecting and measuring the intensity.

2. A measuring apparatus according to claim 1 in which the selectively switching means is an electrooptical crystal.

3. A measuring apparatus according to claims 1 or 2 in which the detection and measuring means comprises a means disposed to receive the transmitted portion of the combined beam for diffusing and spreading its radiation over a predetermined area, a photomultiplier tube connected behind the diffusing means for detecting the combined beam's radiation, and a means coupled to receive an output electrical signal from the photomultiplier tube for processing and displaying the value of the measured intensity.

4. A measuring apparatus according to claim 3 further including a means inserted before the diffusing means for filtering the combined beam to pass a selected optical bandwidth.

5. A method for the selective measurement of the optical intensities of a sample beam having traversed a sample medium, a backscattered beam having been backscattered by the sample medium, a first composite beam composed of the sample beam plus a reference beam having traversed a reference medium, and a second composite beam composed of the backscattered beam plus the reference beam, which comprises:

selective switching the plane of polarization of a collimated, linearly polarized source beam from a first plane to a second orthogonal plane, both planes being parallel to the line of propagation of the source beam;

splitting the source beam into two beams, the first being further physically divided by the sample medium into the backscattered beam and the sample beam as it traverses the sample medium, and the second becoming the reference beam as it traverses the reference medium;

rotating the plane of polarization of the sample beam 90° from the plane of polarization of the backscattered beam;

selectively aligning the plane of polarization of the reference beam parallel to either the plane of polarization of the sample beam or the backscattered beam;

redirecting the backscattered beam, the sample beam and the reference beam in a manner that they are brought together and made colinear in a combined beam;

passing the combined beam through a means for polarization-analyzing which allows transmission of only that portion with the plane of polarization aligned in a predetermined direction; and detecting and measuring the intensity of that portion of the combined beam passed after the polarization analyzing.

6. An apparatus for the selective measurement of the optical intensities of a sample beam having traversed a sample medium, a backscattered beam having been backscattered by the sample medium, a first composite beam composed of the sample beam plus a reference beam having traversed a reference medium, and a second composite beam composed of the backscattered beam plus the reference beam, comprising:

means disposed to receive a collimated, linearly polarized source beam for modulating the plane of polarization of said source beam by switching it at a frequency $f_o$ between two orthogonal planes, each parallel to the line of propagation of the source beam;

a beam splitter disposed to receive and divide the modulated source beam into the sample beam and the reference beam prior to their respective tranverses of the sample and reference media, and similarly disposed to rereceive and combine the sample beam and reference beam after they have traversed the sample and reference media, and also the backscattered beam caused to be reflected back from the sample beam by the sample medium;

a first mirror adjusted to receive and reflect the sample beam back upon itself and toward the beam splitter after it has traversed a predetermined distance within the sample medium;

a first quarter-wave plate installed to transmit the sample beam before and after reflection by the first mirror at a location just before the first mirror and to cause the plane of polarization of the sample beam be rotated 90°;

a second mirror adjusted to receive and reflect the reference beam back upon itself and toward the beam splitter after it has traversed a predetermined distance within the reference medium;

a second quarter-wave plate installed to transmit the reference beam before and after reflection by the second mirror at a location just before the second mirror, said second quarter-wave plate being electrooptically actuated at a frequency of $f_o/2$ causing modulation of the reference beam plane of polarization between orthogonal planes each parallel to the line of propagation of the reference beam;

a polarized analyzer disposed to receive the sample beam, reference beam and backscattered beam following their recombination by the beam splitter, said polarized analyzer being preset to allow passage of those beams with planes of polarization aligned in a select direction; and means disposed to receive the beams passed by the polarized analyzer for detecting and measuring the intensity.

7. A measuring apparatus according to claim 6 in which the first mirror and second mirror are comprised of retroreflectors.

8. A measuring apparatus according to claim 6 in which the modulating means is an electrooptical crystal.

9. A measuring apparatus according to claim 6 in which the detection and measuring means comprises a means disposed to receive the beams passed by the polarized analyzer for diffusing and spreading the beam's radiation over a predetermined area, a photomultiplier tube connected behind the diffusing means for detecting the beam's radiation, and a means coupled to receive an output electrical signal from the photomultiplier tube for processing and displaying the value of the measured intensity.

10. A measuring apparatus according to claim 9 further including a means inserted before the diffusing means for optical bandpass filtering the transmitted beams.

11. A measuring apparatus according to claim 10 further including a stabilized, plane polarized helium-neon laser, as a source of the collimated, linearly polarized source beam.

12. A measuring apparatus according to claims 6, 7, 8, 9, 10 or 11 further including a window located to transmit the sample beam and backscattered beam while serving to simultaneously isolate the sample medium from the remainder of the apparatus.

13. A measuring apparatus according to claim 12 in which the sample path, the first mirror, and the first quarter-wave plate are installed on a wing of an airplane thereupon defining the sample medium as the atmosphere flown through by the airplane, and further including means for heating the first mirror and the first quarter-wave plate to keep them free of moisture.

14. A measuring apparatus according to claim 7 in which the modulating means is an electrooptical crystal.

15. A measuring apparatus according to claim 14 further including a window located to transmit the sample beam and backscattered beam while serving to simultaneously isolate the sample medium from the remainder of the apparatus.

16. A measuring apparatus according to claim 15 in which the sample path, the first retroreflector, and the first quarter-wave plate are installed on a wing of an airplane thereupon defining the sample medium as the atmosphere flown through by the airplane, and further including means for heating the first retroreflector and the first quarter-wave plate to keep them free of moisture.

17. A measuring apparatus according to claims 7, 8, 14, 15, or 16 in which the detection and measuring means comprises a means disposed to receive the beams passed by the polarized analyzer for diffusing and spreading the beam's radiation over a predetermined area, a photomultiplier tube connected behind the diffusing means for detecting the beam's radiation, and a means coupled to receive an output electrical signal from the photomultiplier tube for processing and displaying the value of the measured intensity.

18. A measuring apparatus according to claim 17 further including a means inserted before the diffusing means for optical bandpass filtering the transmitted beams.

19. A measuring apparatus according to claim 18 further including a stabilized, plane polarized helium-neon laser, as a source of the collimated, linearly polarized source beam.

20. A measuring apparatus according to claim 7 in which the detection and measuring means comprises a means disposed to receive the beams passed by the polarized analyzer for diffusing and spreading the beam's radiation over a predetermined area, a photomultiplier tube connected behind the diffusing means for detecting the beam's radiation, and a means coupled to receive an output electrical signal from the photomultiplier tube for processing and displaying the value of the measured intensity.

21. A measuring apparatus according to claim 20 further including a means inserted before the diffusing means for optical bandpass filtering the transmitted beams.

22. A measuring apparatus according to claim 21 further including a stabilized, plane polarized helium-neon laser, as a source of the collimated, linearly polarized source beam.

23. A measuring apparatus according to claims 20, 21 or 22 further including a window located to transmit the sample beam and backscattered beam while serving to simultaneously isolate the sample medium from the remainder of the apparatus.

24. A measuring apparatus according to claim 23 in which the sample path, the first retroreflector, and the first quarter-wave plate are installed on a wing of an airplane thereupon defining the sample medium as the atmosphere flown through by the airplane, and further including means for heating the first retroreflector and the first quarter-wave plate to keep them free of moisture.

* * * * *